US010791963B2

(12) United States Patent
Bae et al.

(10) Patent No.: US 10,791,963 B2
(45) Date of Patent: Oct. 6, 2020

(54) METHOD FOR MEASURING FINGER MOVEMENTS

(71) Applicant: UNIST (ULSAN NATIONAL INSTITUTE OF SCIENCE AND TECHNOLOGY), Ulsan (KR)

(72) Inventors: Joonbum Bae, Ulsan (KR); Yeongyu Park, Incheon (KR); Jeongsoo Lee, Goyang-si (KR)

(73) Assignee: UNIST (ULSAN NATIONAL INSTITUTE OF SCIENCE AND TECHNOLOGY), Ulsan (KR)

( * ) Notice: Subject to any disclaimer, the term of this patent is extended or adjusted under 35 U.S.C. 154(b) by 21 days.

(21) Appl. No.: 16/212,929

(22) Filed: Dec. 7, 2018

(65) Prior Publication Data

US 2019/0104969 A1 Apr. 11, 2019

Related U.S. Application Data

(62) Division of application No. 15/310,569, filed as application No. PCT/KR2015/004398 on Apr. 30, 2015.

(30) Foreign Application Priority Data

May 12, 2014 (KR) ........................ 10-2014-0056528

(51) Int. Cl.
*A61B 5/11* (2006.01)
*A61B 5/00* (2006.01)
*A61B 5/107* (2006.01)

(52) U.S. Cl.
CPC ............... *A61B 5/11* (2013.01); *A61B 5/1114* (2013.01); *A61B 5/1121* (2013.01); *A61B 5/6806* (2013.01); *A61B 5/1071* (2013.01)

(58) Field of Classification Search
CPC ....... A61B 5/11; A61B 5/1114; A61B 5/1116; A61B 5/1123; A61B 5/4528
See application file for complete search history.

(56) References Cited

U.S. PATENT DOCUMENTS 3,641,664 A * 2/1972 Kirkendall ............. H01C 10/40
29/592.1
8,989,902 B1 * 3/2015 Crawford ................... B25J 3/04
700/257

(Continued)

FOREIGN PATENT DOCUMENTS

JP 2004-344180 A 12/2004
JP 2010-082342 A 4/2010

(Continued)

*Primary Examiner* — Daniel L Cerioni
*Assistant Examiner* — Raymond P Dulman
(74) *Attorney, Agent, or Firm* — Rabin & Berdo, P.C.

(57) ABSTRACT

A method for measuring motions of a thumb and fingers, which can relatively easily measure angles at joints of a thumb and fingers within a limited space of the thumb and fingers, using a system that may be lightweight and compact enough not to hinder a natural motion of a hand. To this end, the method measures motions of a thumb and fingers of a user who wears a glove, and includes: attaching first ends of first and second flexible wires to positions of the glove respectively corresponding to middle and proximal phalanxes of each finger; connecting second ends of the first and second flexible wires to a sensing module so that the first and second flexible wires can move forward and backward while maintaining tension thereof in accordance with a motion of the finger; and by the sensing module, measuring moved distances of the first and second flexible wires, wherein rotary angles at corresponding joints in the thumb and fingers are calculated based on the measured moved distances.

8 Claims, 10 Drawing Sheets

Flexed finger (56) References Cited

U.S. PATENT DOCUMENTS

| | | | |
|---|---|---|---|
| 2003/0126755 A1* | 7/2003 | McGorry | A61B 5/1071 33/512 |
| 2006/0282063 A1 | 12/2006 | Gotani | |
| 2007/0132722 A1 | 6/2007 | Kim et al. | |
| 2011/0302694 A1* | 12/2011 | Wang | A61B 5/103 2/160 |
| 2013/0197399 A1* | 8/2013 | Montgomery | A61B 5/1121 600/595 |
| 2013/0289593 A1* | 10/2013 | Hall | B06B 1/0607 606/169 |

FOREIGN PATENT DOCUMENTS

| | | |
|---|---|---|
| JP | 2010-134905 A | 6/2010 |
| KR | 10-2007-0061255 A | 6/2007 |

\* cited by examiner

Schematic of the proposed system

FIG. 3B

Initial position of the finger

FIG. 3C

Flexed finger

FIG. 3D

Neccesisity of a spring

FIG. 4A

Schematic of the proposed system(multi-joint case)

FIG. 4B

Flexed finger

Cross section of the sensing module

FIG. 8B

Backside of the sensing module

FIG. 8C

Manufactured sensing module

METHOD FOR MEASURING FINGER MOVEMENTS

CROSS-REFERENCE TO RELATED APPLICATIONS

This is a divisional application of U.S. application Ser. No. 15/310,569, filed on Nov. 11, 2016, which was a National Stage application of PCT/KR2015/004398, filed on Apr. 30, 2015. Furthermore, this application claims priority to Korean Application No. 10-2014-0056528, filed on May 12, 2014. The disclosure of these U.S. and Korean applications is incorporated herein by reference.

TECHNICAL FIELD

The present invention relates to a system and method of measuring motions of a thumb and fingers, and more particularly to a system and method of measuring motions of a thumb and fingers, which informs relation between positions varied depending on the motions of a thumb and fingers.

BACKGROUND ART

A hand is one of abundant sources in terms of tactile sensing, and it is impossible to achieve elaborate and complicated manipulation without the hand. To develop a wearable system for the hand, an unconstrained hand motion has to be previously analyzed. Accordingly, extensive researches about a simple system for measuring motions of a thumb and fingers have been carried out.

First, a similarity approach using an optical linear encoder (OLE) has been tried, but the encoder attached to a thumb and fingers and a thick and wide wire cable for the optical encoder may interfere with a natural motion of the thumb and fingers.

Further, a 3D magnetic position sensor has been used in measuring angles at joints of a thumb and fingers, and thus three-dimensionally measured motions of the thumb and fingers. However, required peripheral devices may obstruct the unconstrained hand motion.

In addition, an optical fiber sensor has been also used in measuring the angles. The optical fiber sensor is mounted to a glove for the purpose of easy wearing, but the optical sensor has to be carefully bent to measure the angles at the joints. Besides, the mobility of the optical sensor is extremely limited by required peripheral devices such as a laser diode and an optical power system.

By the way, a flexible resistor is commercially available and shows good performance with respect resolution and repeatability. However, the flexible resistor is economically inefficient and difficult to combine with another system such as a hand exoskeleton system.

Like this, the optical encoder, the magnetic position sensor, the optical fiber sensor, the flexible resistor, and the like have been used, but not regarded as a compact and simple measuring system—capable of measuring unconstrained motions of a thumb and fingers—due to a limited space of a hand.

DISCLOSURE

Technical Problem

The present invention is conceived to solve the foregoing problems, and an aspect of the present invention is to provide a system for measuring motions of a thumb and fingers, which can relatively easily measure angles at joints of a thumb and fingers within a limited space of the thumb and fingers, and is lightweight and compact enough not to hinder a natural motion of a hand, and a method of using the same.

Technical Solution

In accordance with one aspect of the present invention, there is provided a system for measuring motions of a thumb and fingers, the system including: a glove which is worn by a user; first and second flexible wires which are movable in accordance with motions of a thumb and fingers, include first ends attached to the glove and have predetermined lengths; and a sensing module which includes first and second linear potentiometers respectively connecting with second ends of the first and second flexible wires and including elastic members for maintaining tension of the flexible wires, wherein the first end of the first flexible wire is attached to a position on the glove corresponding to a position between a first joint and a second joint of a finger, and the first end of the second flexible wire is attached to a position on the glove corresponding to a position between the second joint and a third joint of the finger, wherein angles at the first and second joints are calculated based on changed distances of the attached positions measured by the flexible wires and the linear potentiometers of the sensing module in accordance with a motion of the finger.

The first and second flexible wires and the sensing module may be provided in each of a thumb and fingers.

The sensing module may be placed on a position of the glove corresponding to a back of a hand.

The elastic member of the sensing module may include a linear spring, and the first, second and third joints respectively correspond to a proximal interphalangeal (PIP) joint, a metacarpophalangeal (MCP) joint and a distal interphalangeal (DIP) joint.

In accordance with one aspect of the present invention, there is provided a method of measuring motions of a thumb and fingers of a user who wears a glove, the method including: attaching first ends of first and second flexible wires to positions of the glove respectively corresponding to middle and proximal phalanxes of each finger; connecting second ends of the first and second flexible wires to a sensing module so that the first and second flexible wires can move forward and backward while maintaining tension thereof in accordance with a motion of the finger; and by the sensing module, measuring moved distances of the first and second flexible wires, wherein rotary angles at corresponding joints in the thumb and fingers are calculated based on the measured moved distances.

The sensing module may be placed on a position of the glove corresponding to a back of a hand.

Each tension of the first and second flexible wires is constantly maintained by an elastic member provided in the sensing module, and the elastic member may include a linear spring.

The moved distances of the first and second flexible wires may be respectively measured by first and second linear potentiometers provided in the sensing module.

The sensing module may include a frame made of nylon and by rapid prototyping technology, but there are no limits to the material and technology as long as they have similar effects.

Advantageous Effects

In the system and method of measuring flexion/extension motions of thumb and finger motion according to an embodiment of the present invention, it is possible to relatively easily measure angles at joints of a thumb and fingers within a limited space of the thumb and fingers, and it is lightweight and compact enough not to hinder a natural motion of a hand.

REFERENCE NUMERALS

100 System for measuring motions of a finger and thumbs
10 user wearable glove
20 first and second flexible wires
30 sensing module
40 cylindrical guide

BEST MODE

Embodiments of the present invention will be described in detail with reference to the accompanying drawings. Prior to the description, it will be appreciated that terms and words used in the following description and claims have to be interpreted by not the limited meaning of the typical or dictionary definition, but the meaning and concept corresponding to the technical idea of the present invention on the assumption that the inventor can properly define the concept of the terms in order to describe his/her own invention in the best way.

Further, embodiments described in this specification and elements shown in the drawings are nothing but preferable examples, and do not represent the entirety of the present technical idea. Accordingly, it will be appreciated that they may be replaced by various equivalents and modifications on the filing date of the present invention.

The present invention proposes a system for measuring motions of a thumb and fingers, which employs a linear potentiometer, a flexible wire and a linear spring. The flexible wires are attached to backsides of a thumb and fingers. As the flexible wire moves corresponding to motions of a thumb and fingers, angles at joints are calculated by measuring change in the length of the flexible wire. The linear potentiometer, which has the linear spring for maintaining tension of the wire, is used in measuring the angles at the joints. A proximal interphalangeal (PIP) motion is dependent on a distal interphalangeal (DIP) joint, and therefore only two linear potentiometers are applied to each of the thumb and fingers. This compact sensing module with ten linear potentiometers and springs is attached to a glove. By just wearing such a glove, the motions of the thumb and fingers are easily measured by an easy program interface.

Skeleton Structure of Hand

A hand consists of bones, muscles and ligaments of joints, which are complicatedly combined and determine a direction and range of a hand motion. To accurately measure motions of a thumb and fingers, it is required to understand an anatomical structure of a hand. Below, the anatomical structure of the hand will be described in brief.

Figure 1:
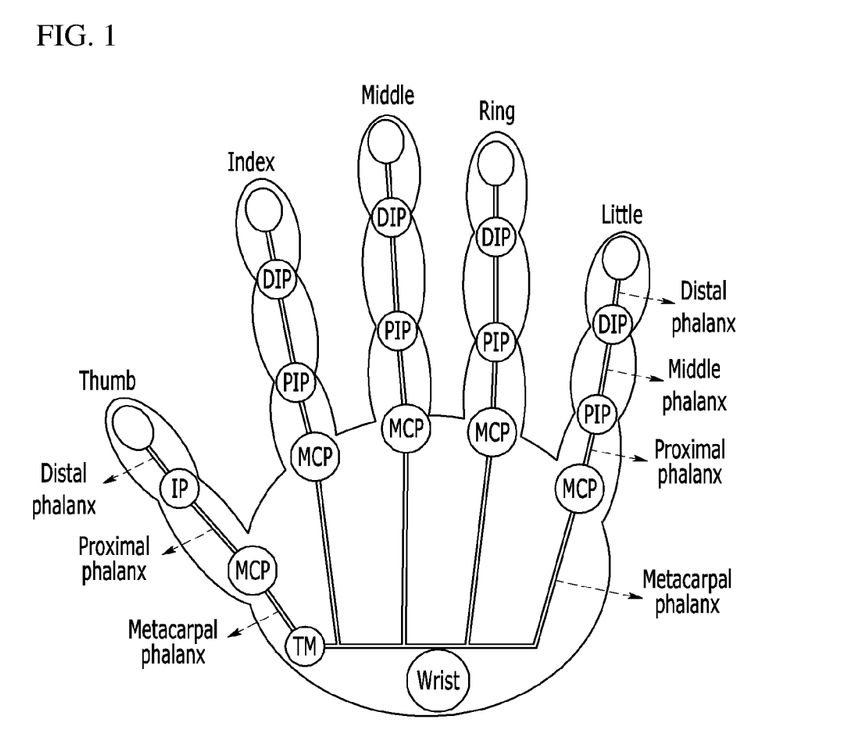
FIG. 1 is an anatomical schematic view of a hand.

The hand motion is carried out by 19 bones, 19 joints and 29 muscles. As shown in FIG. 1, each of the fingers except the thumb includes three bones, i.e. a distal phalanx, a middle phalanx and a proximal phalanx and three joints, i.e. a proximal interphalangeal (PIP) joint, a metacarpophalangeal (MCP) joint and a distal interphalangeal (DIP) joint. The thumb includes two bones, i.e. a distal phalanx and a proximal phalanx, and two joints, i.e. an interphalangeal (IP) joint, and an MCP joint. Metacarpal phalanx bones meet a wrist at carpometacarpal (CMC) joints. The IP joint including the PIP and DIP joints has one degree of freedom for flexion/extension motions, and the MCP joint has two degrees of freedom for flexion/extension and abduction/adduction motions.

To control an object with a hand, the motion of flexion/extension is typically more required than the motion of abduction/adduction. Accordingly, there is a great need of a system for measuring flexion/extension motions of a thumb and fingers without hindering natural motions of the thumb and fingers.

System Elements

Figure 2:
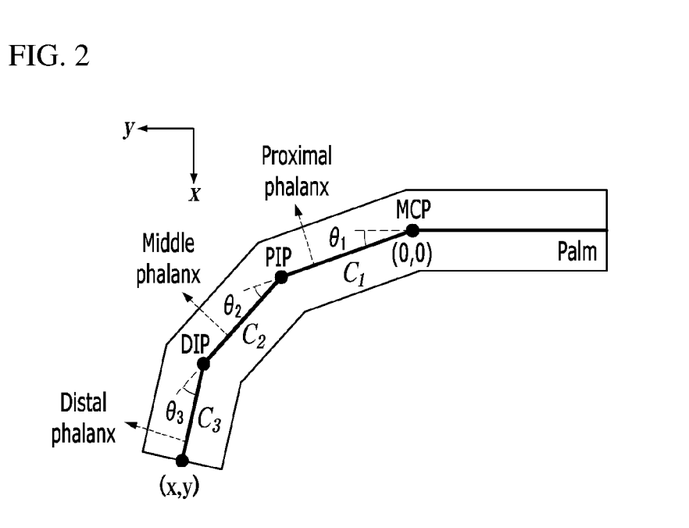
FIG. 2 is a cross-section view of a thumb and fingers.

FIG. 2 shows a cross-section of a finger for a flexion/extension motion. In each of the fingers, the lengths $C_1$, $C_2$ and $C_3$ of the phalanxes are previously measured. When angles of $\theta_1$, $\theta_2$ and $\theta_3$ between joints are measured, a tip position of the finger is expressed as follows.

$$x = C_1 \cos(\theta_1) + C_2 \cos(\theta_2) + C_3 \cos(\theta_3) \quad \text{[Equation 1]}$$

$$y = C_1 \sin(\theta_1) + C_2 \sin(\theta_2) + C_3 \sin(\theta_3) \quad \text{[Equation 2]}$$

As shown in the Equations 1 and 2, only three angles at the joints are needed to describe the flexion/extension motion of each finger. However, a limited space of the thumb makes it difficult to measure the angles at the joints of the finger. Further, a system for measuring the angle has to be lightweight and compact enough not to hinder natural motions of a hand.

As described above, there have been many tries for accurately measuring the joints of the thumb and fingers. That is, in the similarity approach using the optical linear encoder (OLE), the encoder attached to the thumb and fingers and the thick and wide wire cable for the optical encoder may interfere with a natural motion of the thumb and fingers. In the 3D magnetic position sensor 3 for measuring the angles at the joints of the thumb and fingers, required peripheral devices may obstruct the unconstrained hand motion. In the method of using the optical fiber sensor, the optical sensor has to be carefully bent to measure the angles at the joints, and by required peripheral devices such as a laser diode and an optical power system extremely limits the mobility of the optical sensor. In the method of using the flexible resistor, it is economically inefficient and difficult to combine with another system such as a hand exoskeleton system.

According to the present invention, a linear potentiometer with a flexible wire and a linear spring is used for measuring flexion/extension motions of a thumb and fingers. FIGS. 3A to 3D show basic concept of the present invention. For better understanding, an example of only one joint is shown in FIGS. 3A to 3D.

Figure 3A:
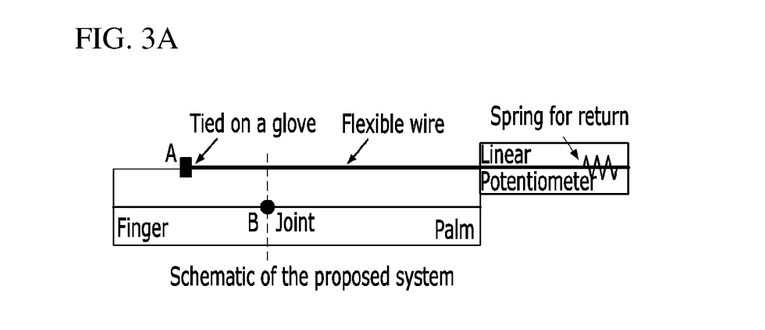
FIGS. 3A to 3D are conception views of a system according to the present invention.
Figure 3B:
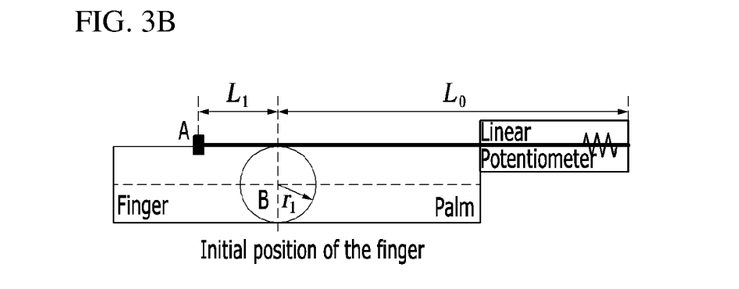

As shown in FIG. 3A, the flexible wire (e.g. a fishing line, etc.) is attached to a glove at a specific position (e.g. 'A') in a thumb and fingers by tying or the like method. Since the joint motions of the thumb and fingers joint motion are regarded as rotary motions with respect to specific joints (e.g. 'B'inside the thumb or finger), the motion with respect to one joint can be expressed as shown in FIG. 3B. As the thumb or finger is crooked, wrinkles at the joint of the thumb or finger are stretched out and thus the attached line moves. The moved distance ΔL is calculated as follows.

$$\Delta L_1 = r_1 \theta_1 \quad [\text{Equation 3}]$$

where, $r_1$ is a diameter of the joint in the thumb or finger, and $\theta_1$ is an angle at the joint.

Figure 3C:
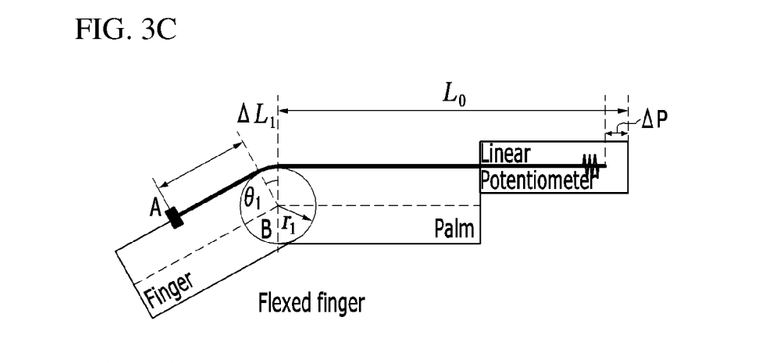

The diameter of the joint in the thumb or finger may be directly measured. The length change $\Delta L_1$ is equal to $\Delta P$ and measured by the linear potentiometer length installed as shown in FIG. 3C. Thus, the angle at the joint is calculated as follows.

$$\theta_1 = \frac{\Delta P}{r_1} \quad [\text{Equation 4}]$$

Figure 3D:
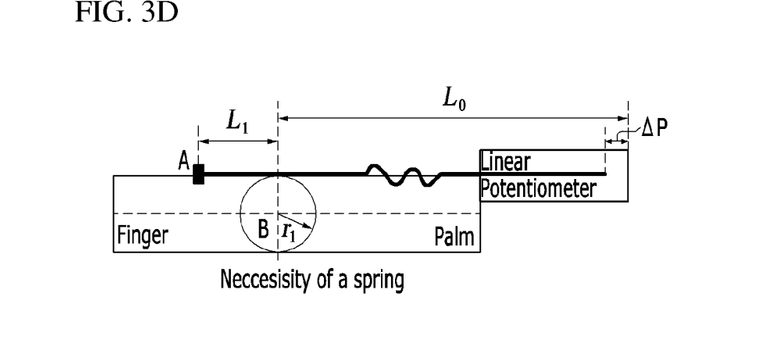

When the thumb of finger is spread out to the initial position, the thumb or finger wire is also returned to the initial position by the spring installed in the potentiometer. If the spring is not given, the flexible wire is loosed as shown in FIG. 3D and therefore the flexion of the thumb or finger can be measured only once by the system. In other words, the spring serves to keep constant tension of the flexible wire in accordance with motions of the thumb or finger.

Prior to description of multi-joint joint cases, dependency of between the joints of the finger has to be discussed. The DIP joint motion is not independently movable, and dependent on the PIP joint. A relationship between the DIP and PIP joints is approximated as follows.

$$\theta_{DIP} = \frac{2}{3} \theta_{PIP} \quad [\text{Equation 5}]$$

where, $\theta_{DIP}$ and $\theta_{PIP}$ are angles at the DIP and PIP joints, respectively.

However, a more accurate relationship is required to measure angles at two joints by measurement at only one PIP joint. By the accurate relationship between the DIP joint and the PIP joint, measurements are carried out only twice with regard to one finger having three degrees of freedom. The accurate relationship between the DIP joint and the PIP joint is experimentally obtained, and this will be described later.

Figure 4A:
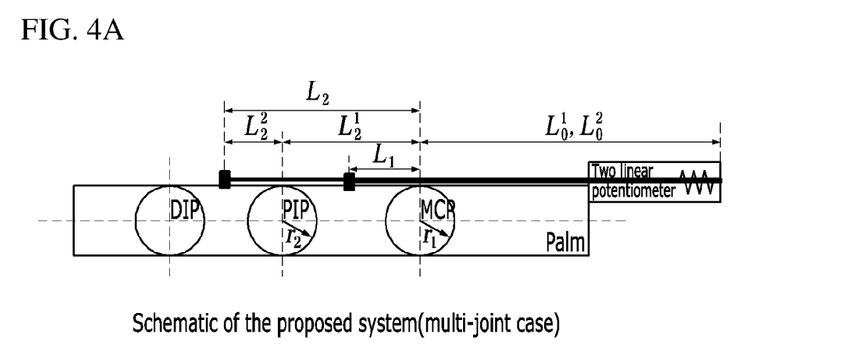
FIGS. 4A and 4B illustrate a system designed according to the present invention.
Figure 4B:
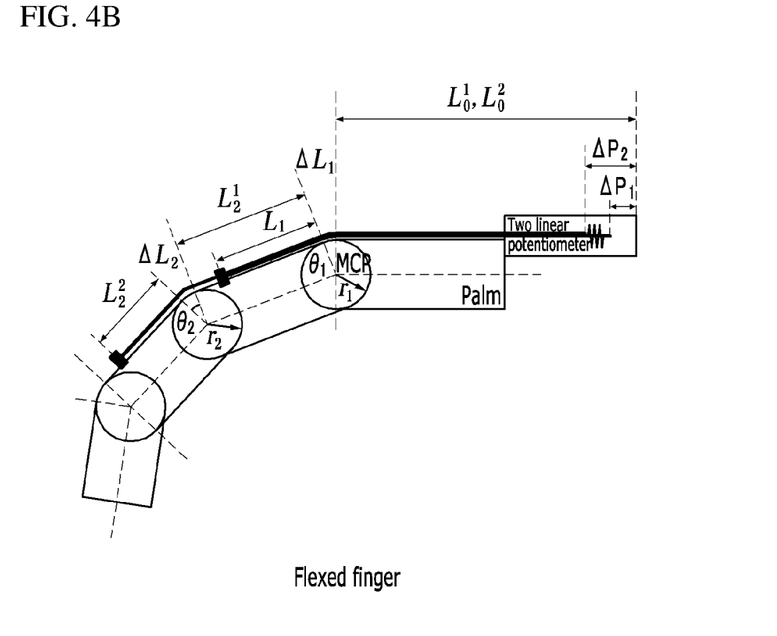

Taking the dependency between the DIP joint and the PIP joint, the present invention is designed as shown in FIGS. 4A and 4B. Like a case of one joint, the angles at the respective joints are measured by the linear potentiometer. Based on such a relationship, the angle at the DIP joint can be obtained by the angle at the PIP joint. Accordingly, only two potentiometers are used in measuring the angles at the PIP and MCP joints, respectively.

If the finger is crooked from FIG. 4A to FIG. 4B, the moved distances $\Delta L_1$ and $\Delta L_2$ of the tied positions are measured by two installed linear potentiometers as follows.

$$\Delta P_1 = \Delta L_1 \quad [\text{Equation 6}]$$

$$\Delta P_2 = \Delta L_1 + \Delta L_2 \quad [\text{Equation 7}]$$

The angles at the joints are calculated as follows.

$$\theta_1 = \frac{\Delta L_1}{r_1} \quad [\text{Equation 8}]$$

$$\theta_2 = \frac{\Delta L_2}{r_2} \quad [\text{Equation 9}]$$

Therefore, the angles at the joints are obtained by the potentiometers as follows.

$$\theta_1 = \frac{\Delta P_1}{r_1} \quad [\text{Equation 10}]$$

$$\theta_2 = \frac{\Delta P_2 - \Delta P_1}{r_2} \quad [\text{Equation 11}]$$

Figure 5:
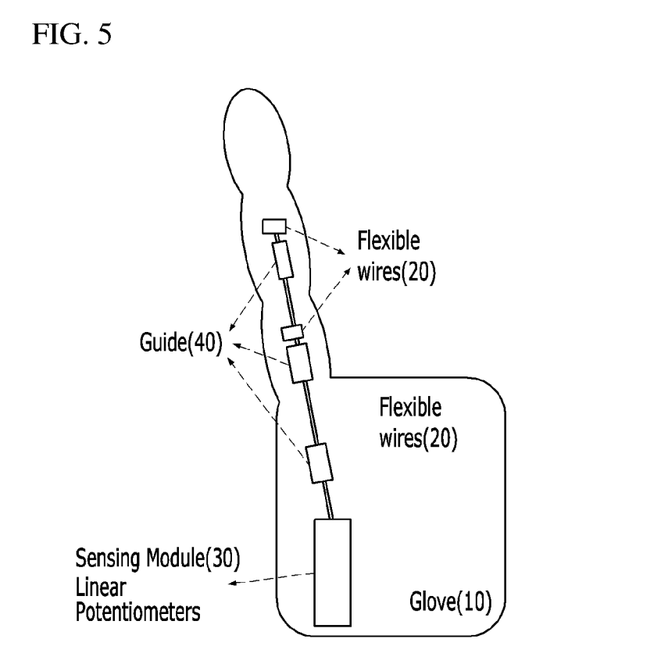
FIG. 5 illustrates a system designed according to the present invention.

According to the present invention, only the changed distances of the tied positions, which can be measured by the flexible wire and the linear potentiometer, are required. One of the advantages in the present invention is that the flexible wire is bendable and thus there are no needs of aligning the wire with the finger. Therefore, a sensing module 30, which includes the potentiometer with the spring, is placed on a back of a hand, and a flexible wire 20 is tied on a glove 10 and connected to the sensing module 30 as shown in FIG. 5. For measurements at the PIP and MCP joints, two flexible wires 20 are used for each of the thumb and fingers, and respectively connected to the middle phalanx and proximal phalanx. In addition, a thin cylindrical guide 40 is mounted to the glove so that the wire can be properly bent.

Test

To test the performance of the system according to the present invention, measured values of the present invention were compared with the measured values of a small wireless inertial measurement unit (IMU) sensor attached to the thumb and fingers. The IMU sensor, which is capable of an angle at orthogonal 3-axial joint, was used in measuring only the flexion/extension motion, and then compared with the measurements of the potentiometer.

Before applying the system according to the present invention to a human's hand, the concept of the present invention was tested using a wooden hand. By the test using the wooden hand, uncertainties of a glove or human hand (e.g. extension of a glove, dependent rotation at each joint, etc.) were decreased.

Figure 6:
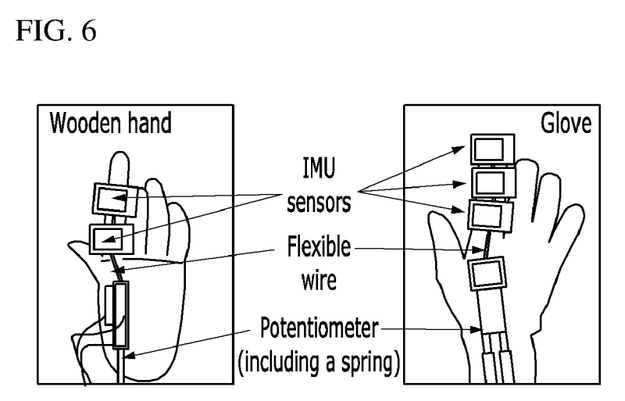
FIG. 6 illustrates a test device.

The IMU sensor and the flexible wire were attached to the wooden hand as shown at the left side in FIG. 6. The IMU sensor was directly bonded to the wooden finger, and the flexible wire was used to connect the wooden finger (between the DIP and PIP joints) and the linear potentiometer having the restoring linear spring. The potentiometer was placed on the back of the wooden hand. In the test, the index finger was crooked at only the PIP joint but not moved at the MCP joint. The signal measured by the potentiometer was converted by the Equation 9 into the angle at the PIP joint. The test results showed that two measured values were matched with each other having an average error of 0.65 degrees.

As mentioned above, the dependency between the DIP and PIP joints will be discussed below, and relation between them will be derived. The motions of the thumb and fingers are generated by combination of flexor digitorum profundus (FDP) and flexor digitorum superficialis (FDS) muscles. Since the FDP simultaneously generates motions at both the PIP and DIP joints, the motions at these joints are coupled. The relation between these motions is known as a linear relation, but a more accurate relation is experimentally obtained as follows.

Figure 7:
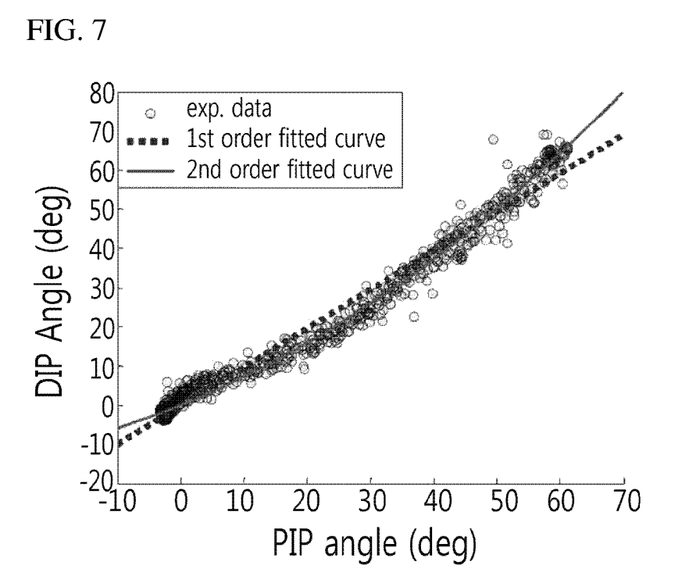
FIG. 7 is a graph of showing a relationship between a DIP joint and a PIP joint.

The angles at the DIP and PIP joints were measured many times by the IMU sensor with respect to different participants. FIG. 7 shows representative results. In the experiments, the participants were requested to freely bend and extend their own thumb and fingers without any constraint. The relation was derived by a curve-fitting method. Average data from the experiments were fitted by first-order and second-order as follows.

$$\theta_{DIP}=0.989\theta_{PIP}-0.230 \qquad \text{[Equation 12]}$$

$$\theta_{DIP}=0.006\theta_{PIP}^2+0.674\theta_{PIP}+0.104 \qquad \text{[Equation 13]}$$

where, $\theta_{DIP}$ and $\theta_{PIP}$ are angles at the DIP and PIP joints, respectively.

Root mean square errors (RMSE) of first-order and second-order cases were 3.104 degrees and 2.251 degrees, respectively. The curved-fitting results showed that the angles at the DIP and PIP joints are not linearly coupled, and the second-order fitting is better than the first-order fitting. However, this is significantly different from the well-known first-order approximation based on the Equation 5.

A simulator for measuring angles at joints of a finger is shown at the right side in FIG. 6. Three IMU sensors were attached to an index finger and measured the angles at the DIP, PIP and MCP joints. Two wires were respectively tied on the proximal phalanx and middle phalanx of the glove and connected to two potentiometers. In the experiment, a palm was kept flat and the index finger was bent forward and backward many times as a typical flexion/extension motion.

The values measured in the potentiometers were converted by the Equations 10 and 11 into angles. All the values obtained by the experiments generally showed that two measuring methods considerably coincided with each other. However, the two measuring methods were a little different in measuring the angle at the DIP joint. This difference may be caused by errors accumulated in measuring the angle at the PIP joint and modeling the relation between the DIP and PIP joints.

Realization of the Invention

Figure 8A:
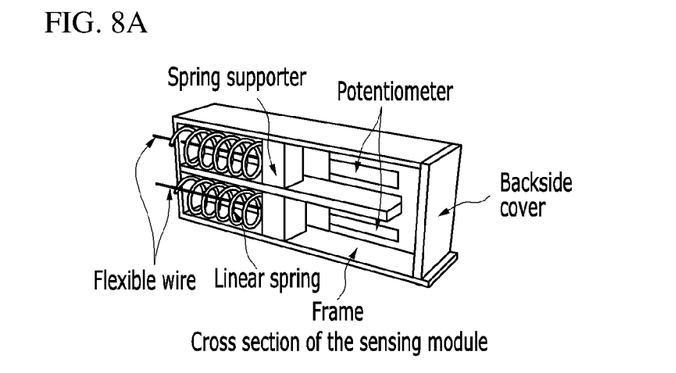
FIGS. 8A to 8C illustrate a sensing module designed according to an embodiment of the present invention.

According to the present invention, ten potentiometers are needed for measuring flexion/extension motions of a thumb and four fingers. To make a compact and lightweight sensing module that does not hinder a natural motion of a hand, a small linear potentiometer having a stroke of 20 mm were used (see FIGS. 8A to 8C). As shown in FIG. 8A, two potentiometers were arranged vertically to reduce the size of the sensing module. The flexible wire was tied on each level of the potentiometer, and connected to the glove through a small hole in a frame. As shown in FIG. 8A, the linear spring designed based on a manual was installed to return the potentiometer to the initial position when the thumb and fingers are extended.

Figure 8B:
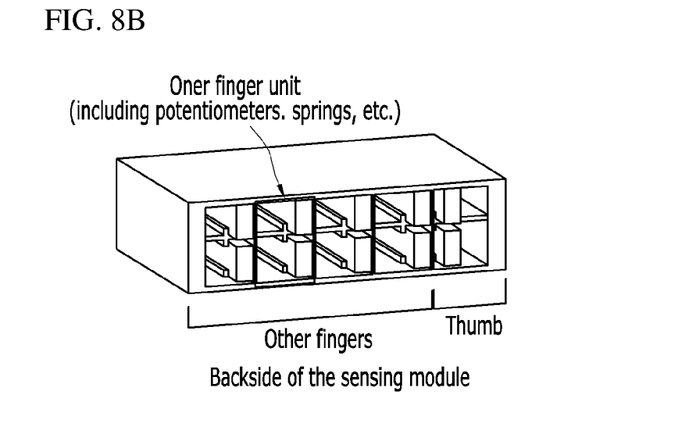
Figure 8C:
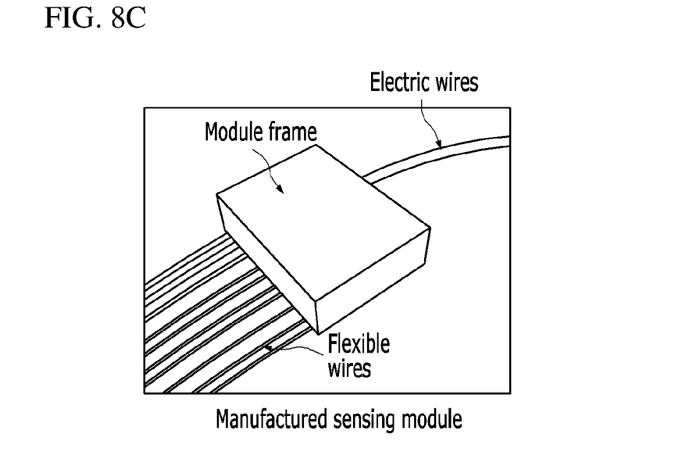
Figure 9:
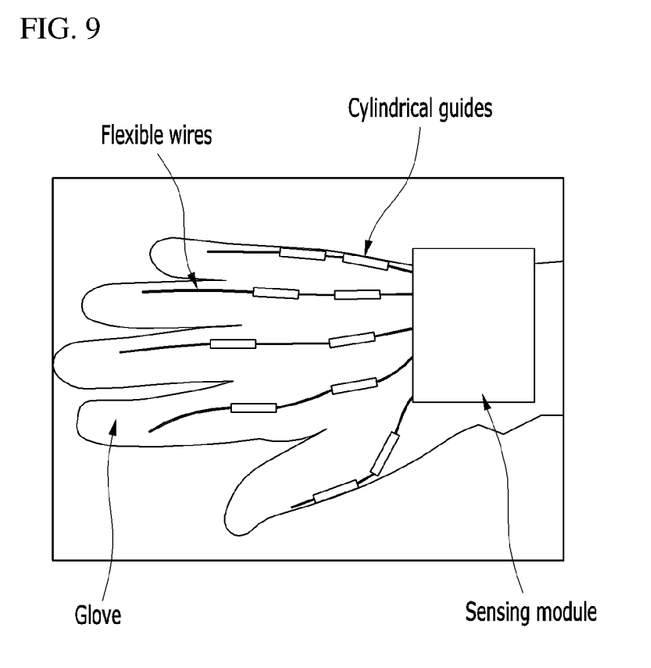
FIG. 9 is a photograph of a wearable sensing glove according to an embodiment of the present invention.

FIG. 8B shows the backside of the sensing module. The potentiometer and the spring were installed through the backside of the sensing module. The frame of the sensing module may be made of various materials/by various methods. In this embodiment, the frame of the sensing module was made of nylon and by rapid prototyping technology. The frame has a size of 45×61×17.4 mm and a weight of 39 g, which is compact enough not to hinder a hand motion. The sensing module is attached to the glove, and a user wears the glove as shown in FIG. 9.

Figure 10:
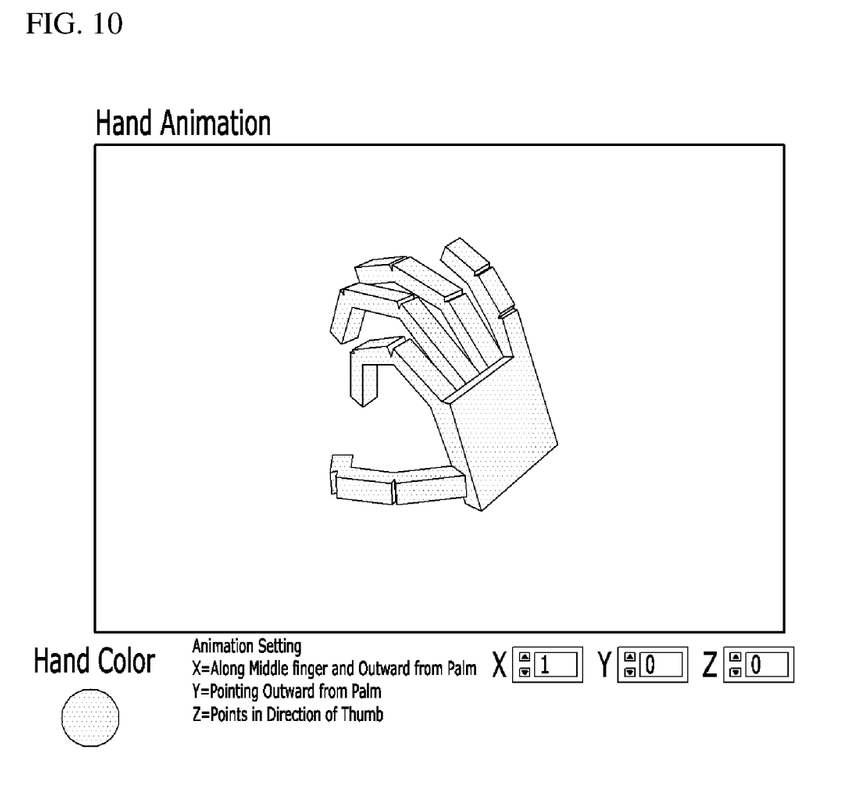
FIG. 10 shows a program interface according to an embodiment of the present invention.

The measured angles at the joints were shown in FIG. 10. In this program, a stiff link body was modeled on a human's hand that has fourteen degrees of freedom—a thumb having two degrees of freedom and four fingers each having three degrees of freedom. This program provides an intuitive interface about a wearable sensing glove.

Although a few exemplary embodiments of the present invention have been shown and described, it will be appreciated by those skilled in the art that changes may be made in these embodiments without departing from the principles and spirit of the invention, the scope of which is defined in the appended claims and their equivalents.

The invention claimed is:
1. A method of measuring motions of a thumb and fingers of a user who wears a glove, the method comprising:
   attaching a first end of a first flexible wire to a position on the glove corresponding to a position between a first joint and a second joint of a first finger;
   attaching a first end of a second flexible wire to a position on the glove corresponding to a position between the second joint and a third joint of the first finger;
   connecting second ends of the first and second flexible wires to a sensing module so that the first and second flexible wires are movable forward and backward while maintaining tension thereof in accordance with a motion of the first finger;
   measuring, by the sensing module, moved distances of the first and second flexible wires; and
   calculating rotary angles of the first joint and the second joint based on the measured moved distances by the following equations:

$$\theta_1 = \frac{\Delta P_1}{r_1}$$

$$\theta_2 = \frac{\Delta P_2 - \Delta P_1}{r_2}$$

where $\theta 1$ is an angle at the first joint, $\theta 2$ is an angle at the second joint, r1 is a diameter of the first joint in the first finger, r2 is a diameter of the second joint in the first finger, $\Delta P1$ is a length change measured by the sensing module based on a moved distance of the first flexible wire, and $\Delta P2$ is a length change measured by the sensing module based on a moved distance of the second flexible wire,
   wherein each finger of the glove has only two flexible wires attached thereto.
2. The method according to claim 1, wherein the sensing module is placed on a position of the glove corresponding to a back of a hand.

3. The method according to claim 1, wherein each tension of the first and second flexible wires is constantly maintained by an elastic member provided in the sensing module.

4. The method according to claim 3, wherein the elastic member comprises a linear spring.

5. The method according to claim 1, wherein the moved distances of the first and second flexible wires are respectively measured by first and second linear potentiometers provided in the sensing module.

6. The method according to claim 2, wherein the moved distances of the first and second flexible wires are respectively measured by first and second linear potentiometers provided in the sensing module.

7. The method according to claim 3, wherein the moved distances of the first and second flexible wires are respectively measured by first and second linear potentiometers provided in the sensing module.

8. The method according to claim 4, wherein the moved distances of the first and second flexible wires are respectively measured by first and second linear potentiometers provided in the sensing module.

* * * * *